United States Patent
Vassiliadis et al.

Patent Number: 5,257,935
Date of Patent: Nov. 2, 1993

[54] DENTAL LASER

[75] Inventors: Arthur Vassiliadis, Mountain View, Calif.; William D. Myers, Birmingham; Terry D. Myers, Farmington Hills, both of Mich.

[73] Assignee: American Dental Laser, Inc., Troy, Mich.

[21] Appl. No.: 343,399

[22] Filed: Apr. 25, 1989

Related U.S. Application Data

[63] Continuation-in-part of Ser. No. 167,739, Mar. 14, 1988, abandoned.

[51] Int. Cl.⁵ .................... A61C 5/00; A61B 17/36
[52] U.S. Cl. ........................ 433/215; 606/14; 606/15
[58] Field of Search .................. 433/215, 229; 128/303.1

[56] References Cited

U.S. PATENT DOCUMENTS

| | | | |
|---|---|---|---|
| 4,170,997 | 10/1979 | Pinnow | 433/114 X |
| 4,273,535 | 6/1981 | Yamamoto et al. | 433/141 X |
| 4,503,853 | 3/1985 | Ota et al. | 433/215 X |
| 4,521,194 | 6/1985 | Myers et al. | 433/215 |
| 4,559,942 | 12/1985 | Eisenberg | 606/18 X |
| 4,679,198 | 7/1987 | Shore et al. | 372/40 X |
| 4,736,745 | 4/1988 | Gluckman | 433/140 X |
| 4,784,135 | 11/1988 | Blum et al. | 128/395 X |
| 4,818,230 | 4/1989 | Myers et al. | 433/215 |
| 4,846,172 | 7/1989 | Berlin | 606/4 |
| 4,852,567 | 8/1989 | Sinofsky | 606/3 |
| 4,854,315 | 8/1989 | Stack et al. | 606/3 |
| 4,887,592 | 12/1989 | Loertscher | 606/5 |

FOREIGN PATENT DOCUMENTS 0198959  10/1986  European Pat. Off. ......... 128/303.1

*Primary Examiner*—Robert P. Swiatek
*Assistant Examiner*—Nicholas D. Lucchesi
*Attorney, Agent, or Firm*—Gifford, Groh, Sprinkle, Patmore and Anderson

[57] ABSTRACT

An apparatus for removing dental enamel and dentin. This apparatus is also capable of cutting soft tissue. The apparatus includes a laser which, when activated, produces a laser pulse having a wavelength of between 1.5 and 3.5 microns, a beam diameter at the target site in the range of 10 to 5,000 microns, a pulse duration of between several picoseconds and several milliseconds, an energy level of between 0.1 millijoules and five joules per pulse, and pulse repetition rates from one pulse per second to 10,000 pulses per second. The pulse is focussed on the dental enamel or dentin thereby reaching high enough energy densities to vaporize the material. In the case of soft tissues, a special tip is used to concentrate the laser on the tissue so that cutting action can be easily executed.

15 Claims, 1 Drawing Sheet

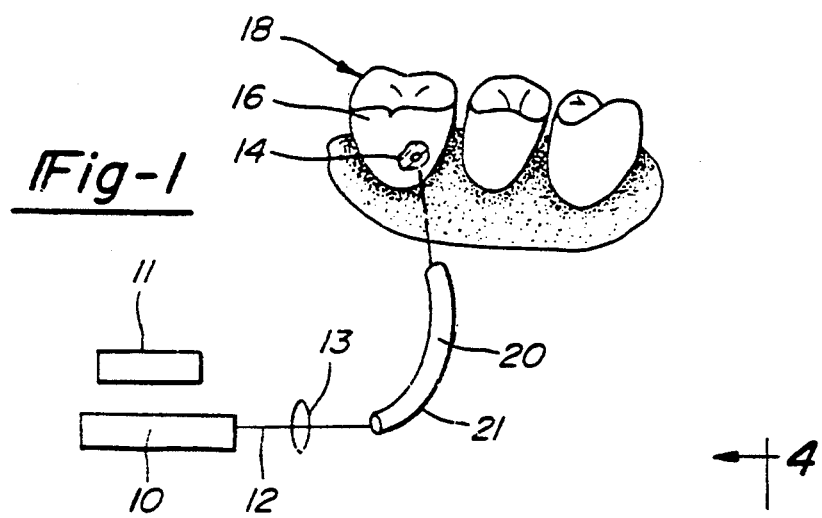
*Fig-1*
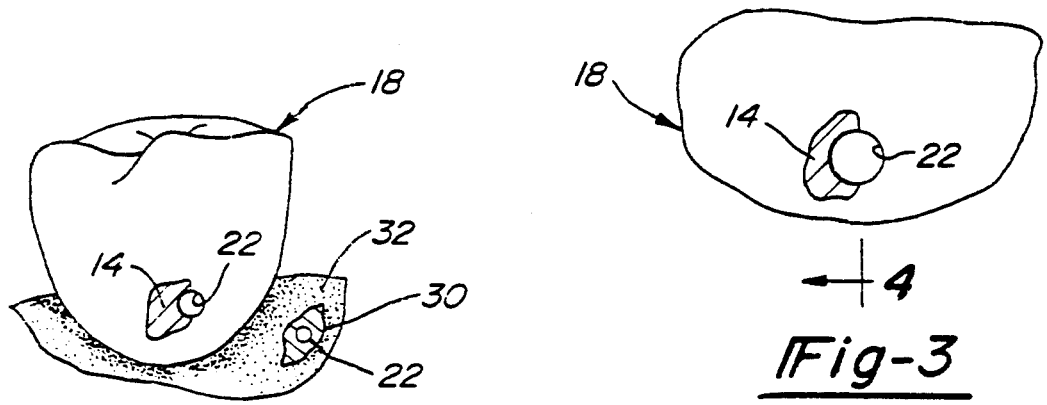
*Fig-2*
*Fig-3*
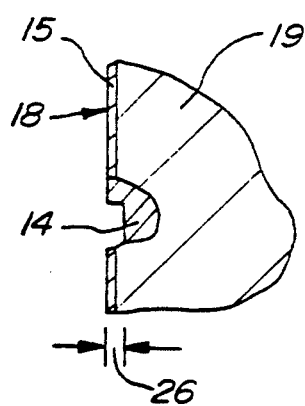
*Fig-4*
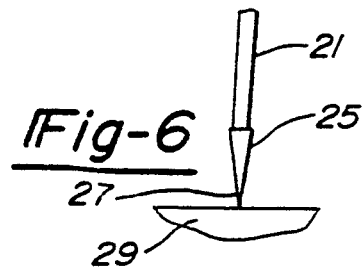
*Fig-6*
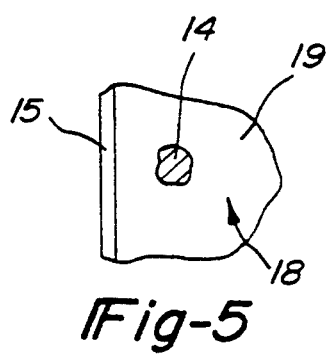
*Fig-5*

DENTAL LASER

CROSS REFERENCE TO RELATED APPLICATIONS

This application is a continuation-in-part of U.S. patent application Ser. No. 167,739, entitled DENTAL LASER, filed on Mar. 14, 1988, now abandoned.

BACKGROUND OF THE INVENTION

I. Field of the Invention

The present invention relates generally to lasers and, more particularly, to a dental laser which is particularly suited for removing dental enamel and dentin, and for cutting soft tissues.

II. Description of the Prior Art

Diseased dental enamel and diseased dentin have traditionally been removed by the dentist by a mechanical drill. On the other hand, diseased soft tissue in the mouth is traditionally removed by cutting with a scalpel, scissors and the like. Both of these methods are uncomfortably painful to the patient, and the results produced have certain drawbacks.

There have, however, been a number of previously known experiments in which teeth have been subjected to laser radiation to determine the alteration, if any, of the physical or chemical properties of the dental enamel. These tests have shown that the hydroxyapatite crystals, that form the enamel, fuse somewhat at the surface when lased and render the enamel more impervious to acids of a type which cause tooth decay.

These previous studies have, however, also concluded that the laser cannot be used to remove tooth decay since the power level necessary for the laser to form an opening in the enamel also significantly heats the tooth and can damage the dental pulp and kill the tooth nerve. For this reason, dental lasers have not been previously used to remove tooth decay or dentin. The lasers that were used previously were operated in different modalities and used different laser materials and were of different wavelengths than those proposed herewith.

In prior U.S. Pat. No. 4,521,194, a method for removing incipient carious lesions from the teeth is disclosed. Such lesions are essentially a surface defect formed on the tooth so that their removal does not require forming an opening in the dental enamel. Furthermore, in that application it was believed that a laser should not be used to form an opening in the dental enamel and dentin for the above-discussed reasons.

U.S. Pat. No. 4,818,230 discloses a method for removing decay that has invaded the dentin as well as removing soft gum tissue in which the peak pulse energy reaches 100 millijoules. In some applications, however, a high energy per pulse is desirable, even if some cooling of the tooth and/or tissues is necessary.

SUMMARY OF THE PRESENT INVENTION

The present invention provides an apparatus for dental procedures in the mouth.

In brief, the present invention comprises a laser and means for activating the laser so that the laser produces a pulsed output having a beam diameter in the range of 10–5000 microns, a pulse duration in the range of several picoseconds to several milliseconds, an energy level of between 0.1 millijoules and five joules per pulse (preferably in the range of 100 millijoules to five joules), and pulse repetition rate of from 1 to 10,000 pulses per second.

In another configuration, a small tip is used to concentrate the radiation so that effective soft tissue cutting can be made. The laser also produces an output pulse having a wavelength in the range of 1.5–3.5 microns. These wavelengths have been shown to be particularly effective for removing dental enamel and dentin. It has also been shown that these wavelengths are highly absorbed by soft tissue in the mouth. The exposures to enamel can be made without significantly heating the tooth or damaging the pulp and the tooth nerve. Furthermore, it has been found that a laser utilizing this wavelength together with the above-mentioned characteristics or laser parameters is capable of effectively and efficiently forming an opening in dental enamel rather than fusing the enamel as taught by the previous studies. Similarly, when used with soft tissues, the laser simultaneously sterilizes the treatment area.

In one form of the invention, the laser is preferably an Erbium doped ytterium-aluminum-garnet (YAG) laser having a wavelength of substantially 2.94 microns. In the second embodiment of the invention, the laser is preferably a Holmium doped crystal laser, having a wavelength of substantially 2.06 microns. Other types of pulsed lasers can, however, alternatively be used.

In use, the laser is repeatedly pulsed until the decay, enamel, dentin or tissue is eradicated. Furthermore, in practice, it has been found that the apparatus of the present invention removes decay, enamel and dentin painlessly and simultaneously sterilizes.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which:

FIG. 1 is a perspective view of a preferred embodiment of the present invention;

FIGS. 2 and 3 are diagrammatic views illustrating the operation of the preferred embodiment of the present invention;

FIG. 4 is a cross-sectional view taken substantially along line 4—4 in FIG. 3;

FIG. 5 is a view similar to FIG. 4 but showing a different type of decay; and

FIG. 6 is a partial side view showing a modification of the present invention.

DETAILED DESCRIPTION OF A PREFERRED EMBODIMENT OF THE INVENTION

With reference first to FIG. 1, a preferred embodiment of the apparatus of the present invention is there-shown and comprises a laser 10 which, upon activation, generates a laser beam 12. A conventional means 11 is employed to energize or activate the laser 10. The laser beam 12 is focussed into a fiber by a lens 13.

The laser 10 produces a pulse output having a beam with a pulse duration in the range of several picoseconds to several milliseconds and an energy of 0.1 millijoules per pulse to five joules per pulse, and pulse repetition rates of from 1 to 10,000 pulses per second. In addition, the laser 10 has a wavelength of between 1.5 and 3.5 microns which has been shown to be particularly effective in eradicating dental enamel and dentin. The laser beam diameter at the target is between 10–5000 microns. It has also been shown that these wavelengths are very effective in cutting soft tissues.

Although any type of laser can be employed, in one form of the invention, the laser is an Erbium doped ytterium-aluminum-garnet (YAG) laser having a wavelength of substantially 2.94 microns. Alternatively, the laser 10 is a Holmium crystal laser having a wavelength of 2.06 microns. In both cases, these wavelengths have proven to be particularly effective for enamel interaction and thus for the eradication of enamel. Enamel 15, of course, is much harder than dentin so that the lasers which eradicate the enamel also are effective in eradicating dentin and decay.

With reference now to FIG. 1, 2 and 4, the laser 10 is employed to remove tooth decay 14 in the tooth 18, which, as shown in FIG. 4, has invaded the tooth dentin 19. A laser output beam 12 is aimed at decay 14 through any conventional delivery system 20, such as an optical fiber 21. A lens 13 is used to focus the output from the laser 10 into one end of the fiber 21 while the other end of the fiber 21 is focussed on the target, i.e. enamel 15, dentin 19, decay and/or soft tissue. A single optical fiber, furthermore, has proven particularly effective for use in dental applications since it may be bent easily to direct or deliver the laser beam to the desired location within the small area of the human mouth.

Other aiming systems can, of course, alternatively be used. For example, as best shown in FIG. 6, a contacting tip 25 may be employed with the optical fiber 21. The tip 25 is typically conical or frustoconical in shape and concentrates the laser energy at its apex 27. The apex 27 then contacts the target 29 (enamel, dentin, decay or soft tissue) in operation. Furthermore, the tip 25 has proven particularly effective for removing soft tissue.

With reference now to FIGS. 2–4, upon activation of the laser 10 by the means 11, the laser eradicates by vaporization the tooth decay 14 and/or enamel and/or dentin 19 in the area 22 of the laser beam impingement a depth 26 (FIG. 4) into the decay 14 in the dentin 19. Thereafter, the laser is reaimed through the delivery system 20 to the remaining portions of the tooth decay 14 and reactivated until the entire decay 14 is eradicated or obliterated from the tooth.

The energy level of the laser is preferably adjustable to produce energy power levels of between 0.1 millijoules and 5 joules which correspondingly varies the depth 26 of the decay 14 obliterated by the laser 10, or the amount of enamel or dentin that is removed. For interacting with tooth decay, which has invaded a tooth to only a relatively shallow depth, relatively low laser energy is used. On the other hand, to remove enamel and dentin, then high energy levels need to be used. It is for this reason that a wide range of energy levels need to be available.

The precise phenomenon which occurs when the tooth is lased and the decay obliterated is not precisely understood due primarily to the extremely short time period involved during the lasing operation. It has been found, however, that both the dental enamel and the dentin is obliterated without significantly heating the tooth and thus without damaging the nerve. Conventional means, such as a water spray, followed by an air jet to blow away most of the water and dry the field, can be used if heating does occur.

With reference now to FIG. 5, in some situations the decay 14 is inside the tooth 18 and is surrounded by healthy dentin 19 and healthy enamel 15. In this case, it is necessary to remove both the healthy enamel 15 and healthy dentin 19 before the decay can be removed by the laser. This has previously been done by drilling.

As best shown in FIG. 2, the laser of the present invention also effectively removes disease 30 from soft tissue 32, such as gum tissue. In order to remove soft tissue, a special tip may be used. The laser uses low energy levels, but high repetition rates of the same wavelength as previously described, and the tip is placed at the diseased portion of the soft tissue and a cutting action is initiated by the means 11. Once activated, the disease portion 30 of the soft tissue 32 is cut away, thus removing the disease and, simultaneously, sterilizing the soft tissue. Repeated activations of the laser may be required to completely eradicate the diseased portion 30 of the soft tissue and the removal of the diseased portion 30 is painlessly accomplished.

In some soft tissue procedures, relatively high energy pulse powers are desirable. Such procedures would include endontic procedures such as root canals, apicoectomies, pulpectomies as well as other soft tissue procedures such as curetage and flap surgery. These higher powers are desirable since they simultaneously remove the diseased tissue and sterilize the treatment area. Cauterization of the work area is also achieved with these higher powers which minimizes bleeding together with the health risks associated with bleeding.

Having described our invention, many modifications thereto will become apparent to those skilled in the art to which it pertains without deviation from the spirit of the invention as defined by the scope of the appended claims.

We claim:

1. Apparatus for removing dental enamel, dentin and/or soft tissue, sterilization in a mouth and/or for endodontic applications at a target site comprising:
   a laser,
   means for activating said laser so that said laser produces a pulsed output having a wavelength of between 1.5 and 3.5 microns, a beam diameter at the target site in the range of 10–5000 microns, a pulse duration in the range of several picoseconds to several milliseconds and an energy of 0.1 millijoules to five joules,
   means for delivering said pulse to dental enamel, dentin and/or soft tissue and/or sterilization site and/or endodontic treatment area to thereby eradicate the dental enamel, dentin and/or soft tissue and/or sterilize and/or perform endodontic procedures.

2. The invention as defined in claim 1 wherein the laser has a pulse repetition rate of 1 to 10,000 pulses per second.

3. The invention as defined in claim 1 wherein said laser is a yttrium-aluminum-garnet (YAG) laser.

4. The invention as defined in claim 1 wherein said laser is a Holmium doped laser.

5. The invention as defined in claim 4 wherein said laser has a wavelength of substantially 2.06 microns.

6. The invention as defined in claim 4 wherein said laser is a glass laser.

7. The invention as defined in claim 4 wherein said laser is a crystal laser.

8. The invention as defined in claim 1 wherein said laser is an Erbium doped laser.

9. The invention as defined in claim 8 wherein said laser has a wavelength of substantially 2.94 microns.

10. The invention as defined in claim 8 wherein said laser is a glass laser.

11. The invention as defined in claim 8 wherein said laser is a crystal laser.

12. The invention as defined in claim 1 wherein said delivering means comprises means for focussing said pulse on one end of an optical fiber strand.

13. The invention as defined in claim 12 wherein comprising a contact tip adjacent the other end of said strand.

14. The invention as defined in claim 13 wherein said tip is conical in shape.

15. The invention as defined in claim 12 wherein at least a portion of said optical fiber strand is flexible.

* * * * *